(12) United States Patent
Ishinabe et al.

(10) Patent No.: US 10,932,665 B2
(45) Date of Patent: Mar. 2, 2021

(54) OPHTHALMOLOGIC MICROSCOPE SYSTEM

(71) Applicant: KABUSHIKI KAISHA TOPCON, Tokyo (JP)

(72) Inventors: Ikuo Ishinabe, Saitama (JP); Michiko Nakanishi, Tokyo (JP); Satoshi Yamamoto, Saitama (JP)

(73) Assignee: KABUSHIKI KAISHA TOPCON, Tokyo (JP)

( * ) Notice: Subject to any disclaimer, the term of this patent is extended or adjusted under 35 U.S.C. 154(b) by 557 days.

(21) Appl. No.: 15/735,998

(22) PCT Filed: Feb. 3, 2016

(86) PCT No.: PCT/JP2016/053286
§ 371 (c)(1),
(2) Date: Dec. 13, 2017

(87) PCT Pub. No.: WO2017/002382
PCT Pub. Date: Jan. 5, 2017

(65) Prior Publication Data
US 2018/0168447 A1 Jun. 21, 2018

(30) Foreign Application Priority Data

Jun. 30, 2015 (JP) ................. 2015-132088

(51) Int. Cl.
*A61B 3/13* (2006.01)
*A61B 3/10* (2006.01)
(Continued)

(52) U.S. Cl.
CPC .............. *A61B 3/13* (2013.01); *A61B 3/0008* (2013.01); *A61B 3/10* (2013.01); *A61B 3/102* (2013.01); *A61B 3/14* (2013.01); *A61F 9/008* (2013.01)

(58) Field of Classification Search
CPC ... A61B 3/0008; A61B 3/0025; A61B 3/0041; A61B 3/005; A61B 3/0058;
(Continued)

(56) References Cited

U.S. PATENT DOCUMENTS 4,601,550 A 7/1986 Yoshino et al.
4,702,570 A 10/1987 Yoshino et al.
(Continued)

FOREIGN PATENT DOCUMENTS

EP 2829219 A1 1/2015
JP S60-035708 A 2/1985
(Continued)

OTHER PUBLICATIONS

International Search Report and Written Opinion dated May 10, 2016, in connection with International Patent Application No. PCT/JP2016/053286, 8 pgs.
(Continued)

*Primary Examiner* — James C. Jones
(74) *Attorney, Agent, or Firm* — Chiesa Shahinian & Giantomasi PC

(57) ABSTRACT

An illumination system of an ophthalmologic microscope system projects illumination light onto a patient's eye. A light receiving system guides returning light of the illumination light to an image sensor. A display controller controls a display device to display an image obtained by the image sensor. A magnification changing unit changes display magnification of the image. An interference optical system detects interference light generated from returning light of measurement light from the eye and reference light. An optical scanner is used to scan the eye with the measurement light. An OCT data generation unit processes a detection result of the interference light to generate data. A condition setting unit sets a projection condition of the measurement (Continued)

light in accordance with change in the display magnification. An OCT controller controls the interference optical system and/or the optical scanner based on the projection condition.

22 Claims, 14 Drawing Sheets

(51) Int. Cl.
*A61B 3/00* (2006.01)
*A61F 9/008* (2006.01)
*A61B 3/14* (2006.01)

(58) Field of Classification Search
CPC ......... A61B 3/0075; A61B 3/10; A61B 3/102; A61B 3/1005; A61B 3/1025; A61B 3/107; A61B 3/117; A61B 3/12; A61B 3/1225; A61B 3/1241; A61B 3/13; A61B 3/132; A61B 3/1233; A61B 3/135; A61B 3/14; A61B 3/145; A61B 3/18; A61B 5/0059; A61B 5/0066; A61B 5/026; A61B 5/489; A61B 5/6821; A61B 90/20; A61B 90/30; A61F 9/008; A61F 2009/00897; A61F 9/007; A61F 2009/00851; G01B 9/02; G01B 9/0203; G01B 9/02004; G01B 9/02044; G01B 9/02068; G01B 9/02083; G01B 9/02089; G01B 9/02091; G01B 11/2441; G01B 2290/65; G02B 15/14; G02B 26/101; G02B 29/105; G02B 27/0012; G02B 27/0955; G02B 27/10; G02B 27/14; G02B 21/0004; G02B 21/0012; G02B 21/0056; G02B 21/025; G02B 21/08; G02B 21/082; G02B 21/20; G02B 21/22; G06F 19/00; G06F 19/34; G01N 2021/1787; G06T 2210/41
USPC ....... 351/200, 205, 206, 208, 209, 210, 211, 351/221, 246; 356/450, 479, 495, 496, 356/497, 498, 511; 345/629; 348/78; 600/425; 702/172
See application file for complete search history.

(56) References Cited

U.S. PATENT DOCUMENTS

| | | | |
|---|---|---|---|
| 8,922,882 B2 | 12/2014 | Hauger et al. | |
| 2007/0047072 A1* | 3/2007 | Zimmer | G02B 21/22 359/377 |
| 2011/0080561 A1* | 4/2011 | Hayashi | A61B 3/102 351/206 |
| 2011/0228218 A1 | 9/2011 | Hauger et al. | |
| 2013/0188129 A1 | 7/2013 | Inoue | |
| 2014/0024949 A1 | 1/2014 | Wei et al. | |
| 2015/0077707 A1 | 3/2015 | Hauger et al. | |
| 2015/0077708 A1 | 3/2015 | Hauger et al. | |
| 2015/0313466 A1 | 11/2015 | Yoshida | |
| 2016/0302738 A1 | 10/2016 | Yoshida et al. | |
| 2016/0310024 A1 | 10/2016 | Yoshida et al. | |
| 2017/0188819 A1 | 7/2017 | Hauger et al. | |
| 2017/0188820 A1 | 7/2017 | Hauger et al. | |

FOREIGN PATENT DOCUMENTS

| | | |
|---|---|---|
| JP | 2011-04877 A | 1/2011 |
| JP | 2012-509729 A | 4/2012 |
| JP | 2013-150697 A | 8/2013 |
| JP | 2013-184018 A | 9/2013 |
| JP | 2014-112165 A | 6/2014 |
| JP | 2014-523537 A | 9/2014 |

OTHER PUBLICATIONS

Notice of Reasons for Refusal dated Jan. 28, 2020, in connection with Japanese Patent Application No. 2019-046746, filed Mar. 14, 2019, 14 pgs.

* cited by examiner

FIG. 6A

| DISPLAY MAGNIFICATION | PROJECTION CONDITION |
|---|---|
| 4 | SCAN SIZE = $A_0$, SCAN INTERVAL = $B_0$ |
| 5 | SCAN SIZE = $A_0 \times 4/5$, SCAN INTERVAL = $B_0 \times 4/5$ |
| 6 | SCAN SIZE = $A_0 \times 2/3$, SCAN INTERVAL = $B_0 \times 2/3$ |
| 7 | SCAN SIZE = $A_0 \times 4/7$, SCAN INTERVAL = $B_0 \times 4/7$ |
| ... | ... |

| CHANGING RATIO OF DISPLAY MAGNIFICATION | PROJECTION CONDITION |
|---|---|
| 1.5 | SCAN SIZE × 2/3, SCAN INTERVAL × 2/3 |
| 2.0 | SCAN SIZE × 1/2, SCAN INTERVAL × 1/2 |
| 2.5 | SCAN SIZE × 2/5, SCAN INTERVAL × 2/5 |
| 3.0 | SCAN SIZE × 1/3, SCAN INTERVAL × 1/3 |
| ... | ... |
| ... | ... |

| SITE OF EYE | PROJECTION CONDITION |
|---|---|
| ONH | SCAN PATTERN=CIRCLE SCAN |
| MACULA | SCAN PATTERN=3D SCAN |
| ... | ... |
| ... | ... |

221d

OPHTHALMOLOGIC MICROSCOPE SYSTEM

CROSS-REFERENCE TO RELATED APPLICATIONS

This application is a national stage (under 35 U.S.C. 371) of International Patent Application No. PCT/JP2016/053286, filed Feb. 3, 2016, claiming priority to Japanese Patent Application No. 2015-132088, filed Jun. 30, 2015, both of which are herein incorporated by reference in their entirety.

TECHNICAL FIELD

Embodiments described herein relate generally to an ophthalmologic microscope system.

BACKGROUND

Various kinds of microscopes are utilized for magnified observation of an eye in the field of ophthalmology. Examples of such ophthalmologic microscopes include slit lamp microscopes and surgical microscopes. There are ophthalmologic microscopes that include an image sensor for imaging an eye, and those that include a binocular optical system that provides binocular disparity for stereoscopic observation.

The ophthalmologic microscopes may be used in combination with another ophthalmologic apparatus. For example, a system is known in which an optical coherence tomography (OCT, hereinafter) apparatus is combined with an ophthalmologic microscope. The OCT apparatus is utilized for, for example, acquiring cross sectional images of an eye, acquiring three dimensional images of an eye, measuring the sizes of ocular tissues (the thickness of the retina), and acquiring functional information on an eye (the blood flow information).

Such a system includes an observation system that is provided with an optical zoom mechanism. The optical zoom mechanism includes a movable lens for changing the focal length. The movable lens scales up and down an observation image. In addition, the OCT apparatus includes a scanning mechanism. The scanning mechanism changes the traveling direction of the light (measurement light) to be projected onto an eye in order to scan the eye.

Microscopes having the digital zoom function are also known. The digital zoom is a function of magnifying a part of a digital image acquired by an image sensor.

SUMMARY OF THE EMBODIMENTS

The object of the present invention is to provide an ophthalmologic microscope system capable of linking the digital zoom of microscope observation and the OCT scan to each other.

An ophthalmologic microscope system according to an embodiment includes an illumination system, a light receiving system, a display controller, a magnification changing unit, an interference optical system, an optical scanner, an OCT data generation unit, a condition setting unit, and an OCT controller. The illumination system is configured to project illumination light onto a patient's eye. The light receiving system is configured to guide returning light of the illumination light that has been projected onto the patient's eye to an image sensor. The display controller is configured to control a display device to display an image based on an output from the image sensor. The magnification changing unit is configured to change display magnification of the image by processing the output from the image sensor. The interference optical system is configured to split light from an OCT light source into measurement light and reference light and detect interference light generated from returning light of the measurement light from the patient's eye and the reference light. The optical scanner is configured to scan the patient's eye with the measurement light. The OCT data generation unit is configured to process a detection result of the interference light to generate data. The condition setting unit is configured to set a projection condition of the measurement light in accordance with change in the display magnification performed by the magnification changing unit. The OCT controller is configured to control at least one of the interference optical system and the optical scanner based on the projection condition set.

According to the ophthalmologic microscope system of the embodiment, it is possible to link the digital zoom of microscope observation and the OCT scan to each other.

BRIEF DESCRIPTION OF THE DRAWINGS

FIG. 6A is a schematic diagram illustrating an example of the configuration of the ophthalmologic microscope system according to the embodiment.

FIG. 6B is a schematic diagram illustrating an example of the configuration of the ophthalmologic microscope system according to the embodiment.

FIG. 6C is a schematic diagram illustrating an example of the configuration of the ophthalmologic microscope system according to the embodiment.

DETAILED DESCRIPTION OF THE EMBODIMENTS

Exemplary embodiments of an ophthalmologic microscope system according to the present invention will be described in detail with reference to the drawings. The contents of the documents cited in the present specification and any known techniques can be incorporated into the embodiments of the present invention.

An ophthalmologic microscope system is used for observing (and photographing) a magnified image of the patient's eye for a diagnosis, treatment and/or surgery in the field of ophthalmology. The site to be observed may be an arbitrary site of the patient's eye. For example, the site to be observed may be any site in the anterior segment such as the cornea, the corner angle, the vitreous body, the crystalline lens, or the ciliary body, and/or may be any site in the posterior segment such as the retina, the choroid, or the vitreous body. The site to be observed may also be any surrounding site of the eye such as the eyelid or the eye socket. The ophthalmologic microscope system includes an OCT function in addition to the function for magnified observation of the patient's eye.

The ophthalmologic microscope system of the embodiment described below includes a Greenough stereo microscope. However, in other embodiments, an ophthalmologic microscope system may include a Galilean stereo microscope. The Greenough stereo microscope is characterized in that the left and right optical systems include individual objective lenses and that the left and right optical axes are non-parallel to each other. The Greenough stereo microscope has the advantages of being able to easily obtain a stereoscopic image, and of having a high degree of flexibility in the design. On the other hand, the Galilean stereo microscope is characterized in that the left and right optical systems have a common objective lens, and that the left and right optical axes are parallel to each other. The Galilean stereo microscope has the advantages of being able to easily combine other optical systems and/or optical elements.

Figure 1:
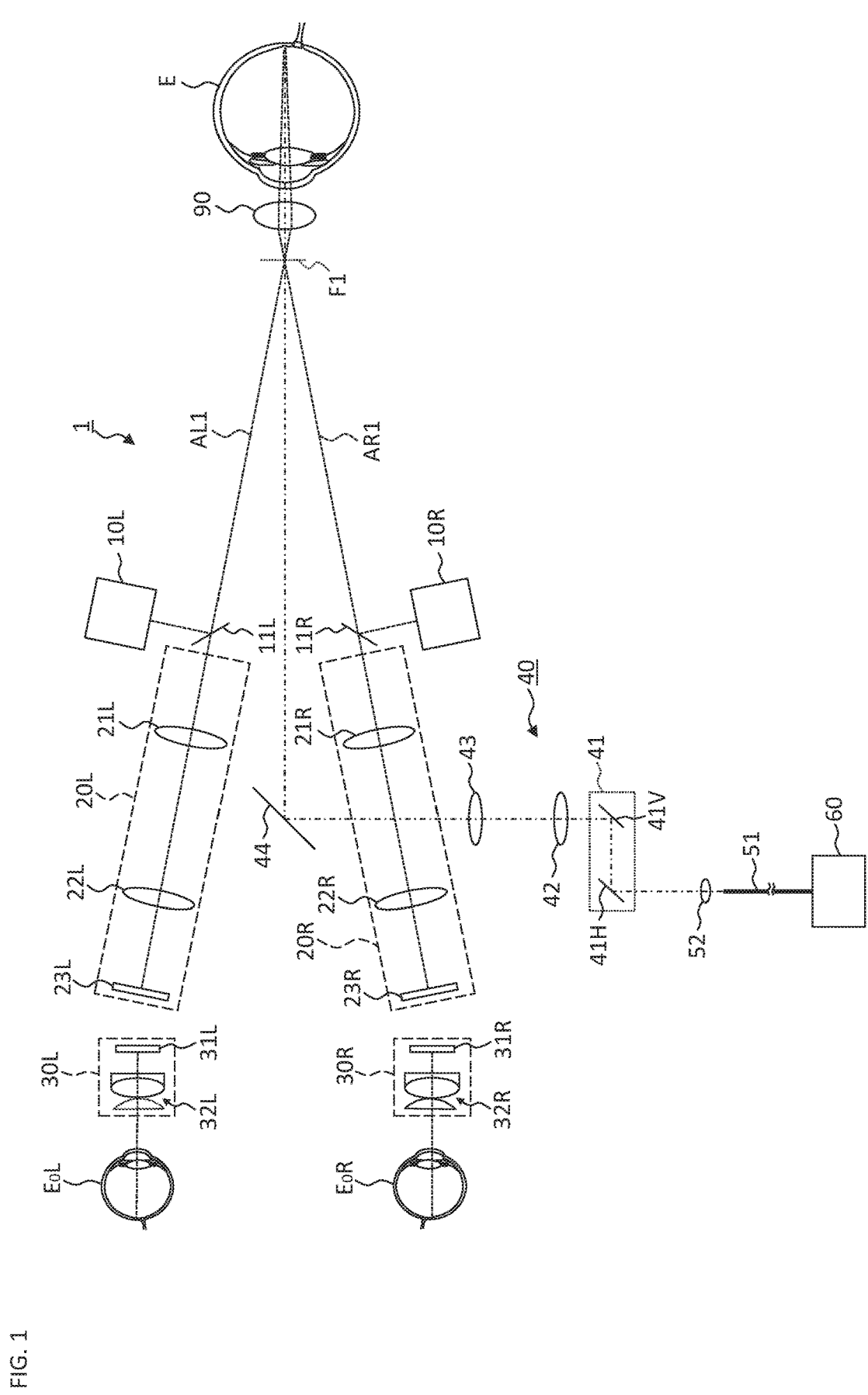
FIG. 1 is a schematic diagram illustrating an example of the configuration of the ophthalmologic microscope system according to the embodiment.
Figure 2:
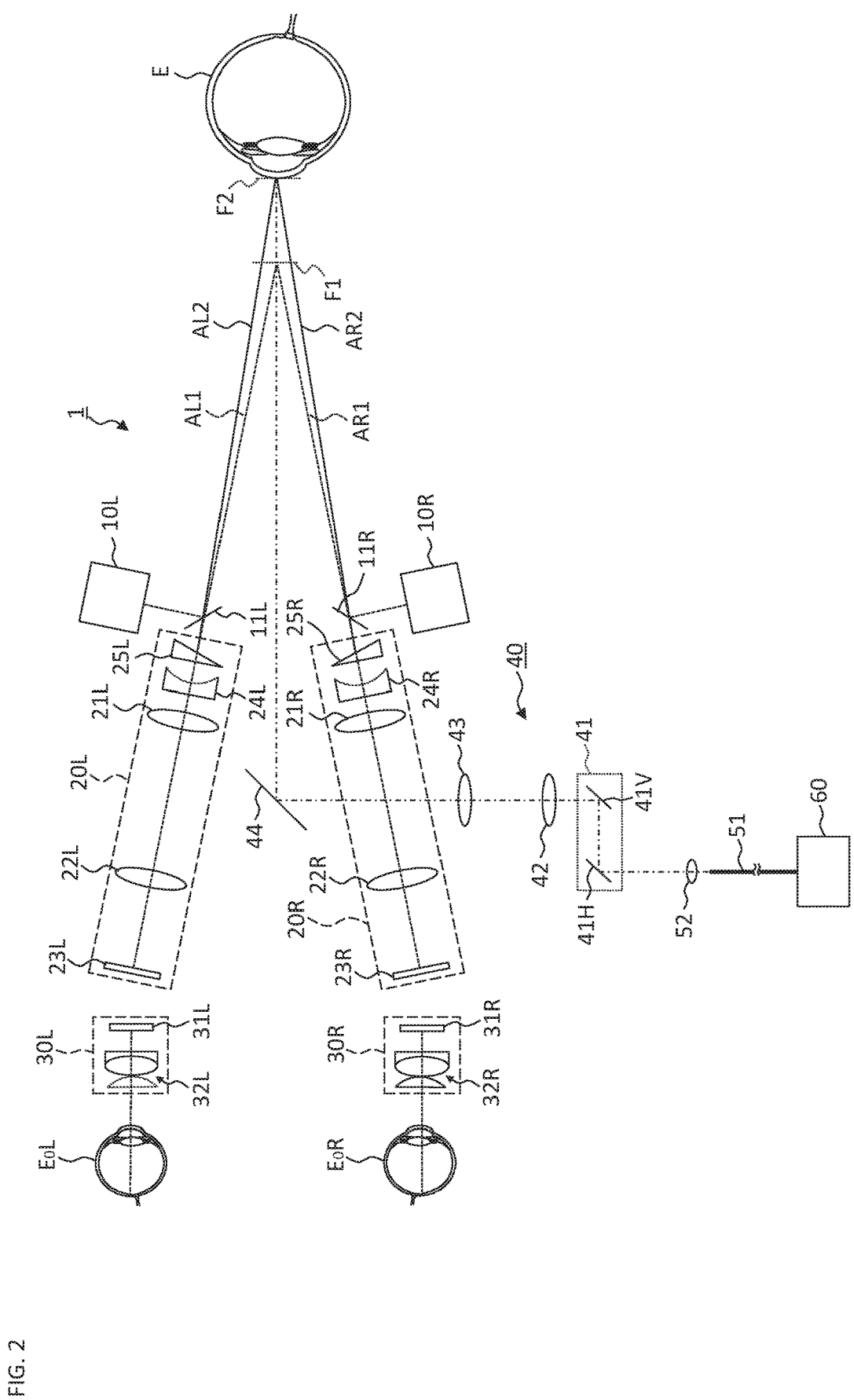
FIG. 2 is a schematic diagram illustrating an example of the configuration of the ophthalmologic microscope system according to the embodiment.
Figure 3:
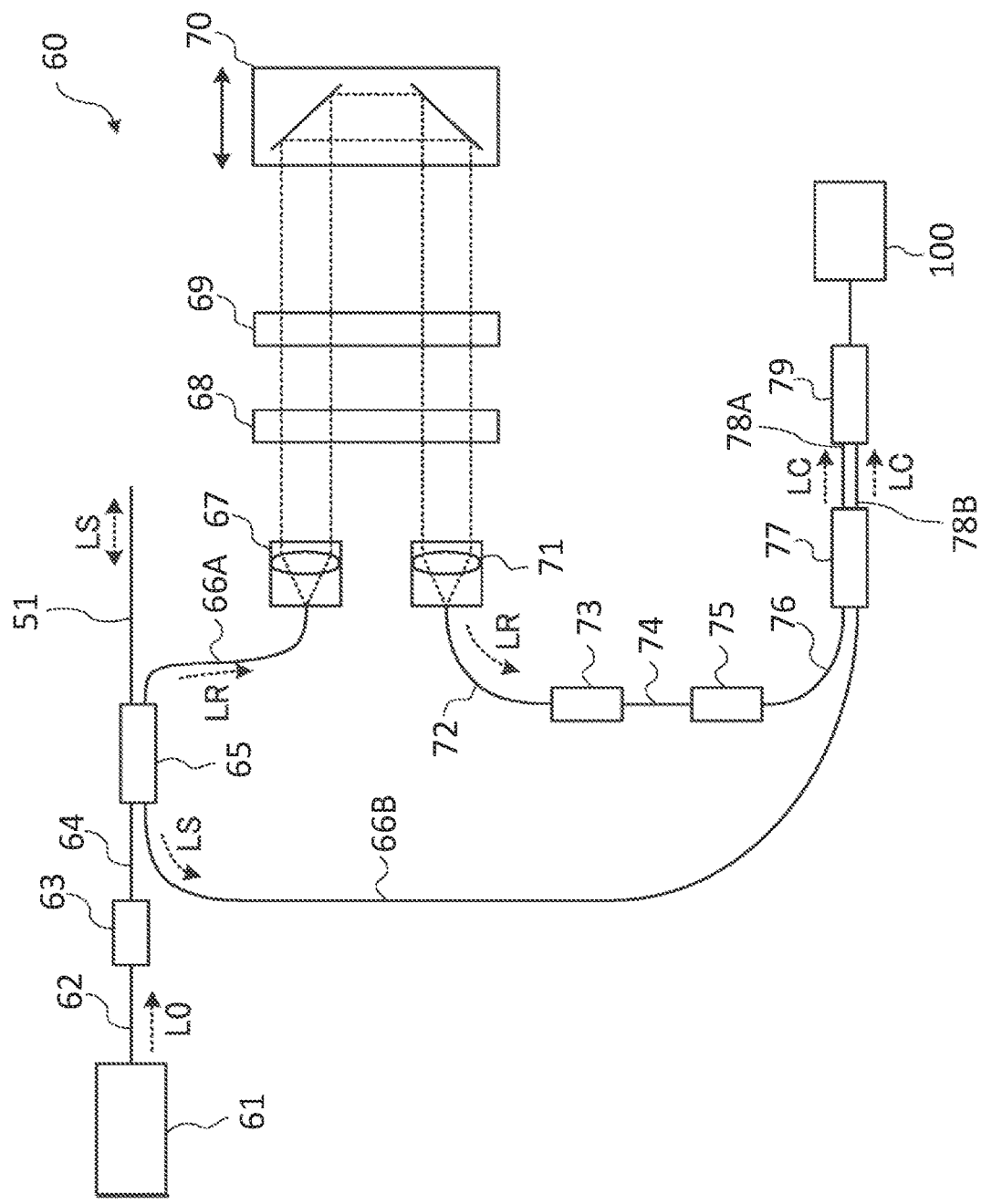
FIG. 3 is a schematic diagram illustrating an example of the configuration of the ophthalmologic microscope system according to the embodiment.
Figure 4:
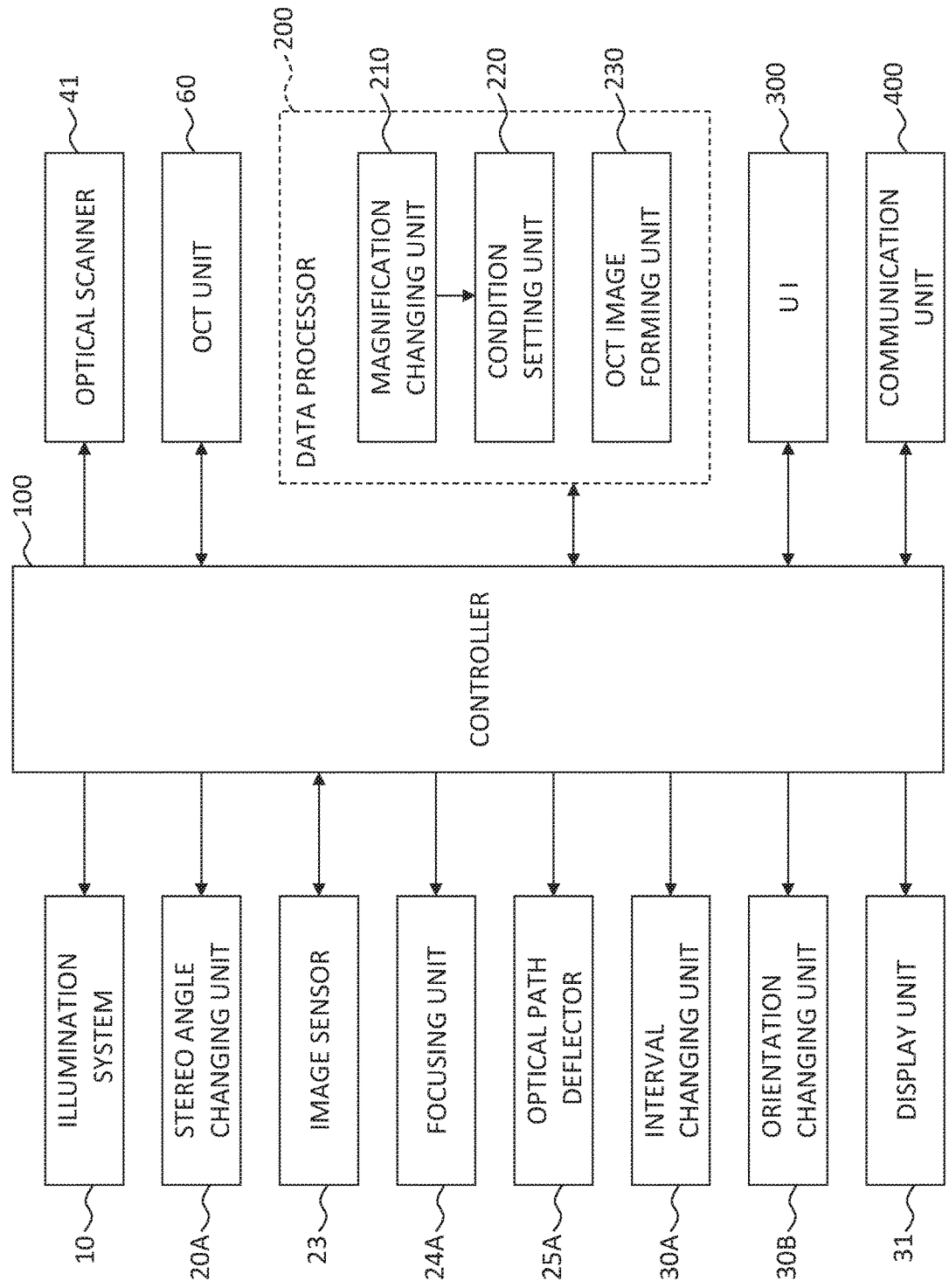
FIG. 4 is a schematic diagram illustrating an example of the configuration of the ophthalmologic microscope system according to the embodiment.
Figure 5:
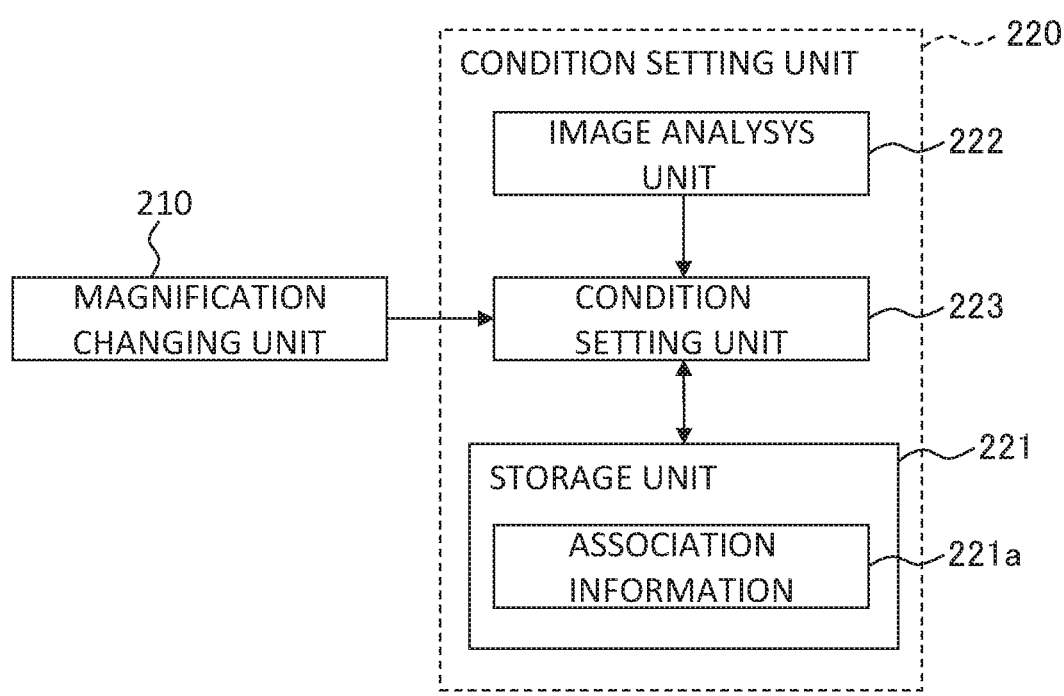
FIG. 5 is a schematic diagram illustrating an example of the configuration of the ophthalmologic microscope system according to the embodiment.

FIG. 1 to FIG. 5 show a configuration of the ophthalmologic microscope system according to the embodiment. FIG. 1 to FIG. 3 show a configuration of the optical system. FIG. 1 shows an optical system applied when observing the posterior eye segment, and FIG. 2 shows an optical system applied when observing the anterior eye segment. FIG. 3 shows an optical system for providing the OCT function. FIG. 4 and FIG. 5 show a configuration of the processing system. FIG. 6A to FIG. 6C show information pre-stored in the processing system.

The ophthalmologic microscope system 1 includes the illumination system 10 (10L and 10R), the light receiving system 20 (20L and 20R), the eyepiece system 30 (30L and 30R), the projection system 40, and the OCT unit 60. When observing the posterior eye segment (the retina, etc.), the front lens 90 is disposed right in front of the patient's eye E. It is possible to use a contact lens or the like instead of the front lens 90 of a non-contact type as shown in FIG. 1. When observing the corner angle, it is possible to use a contact mirror (a triple mirror, etc.) or the like.

The illumination system 10 projects illumination light onto the patient's eye E. Although not shown, the illumination system 10 includes a light source that emits illumination light, a diaphragm that defines an illumination field, a lens system, and the like. The configuration of the illumination system may be similar to conventional ophthalmic apparatuses (for example, a slit lamp microscope, a fundus camera, a refractometer, etc.).

The illumination systems 10L and 10R of the present embodiment are configured coaxially with the light receiving systems 20L and 20R, respectively. More specifically, the beam splitter 11L, which may be a half mirror, is obliquely provided in the left light receiving system 20L for acquiring an image to be presented to the left eye $E_OL$ of the observer. The beam splitter 11L couples the optical path of the left illumination system 10L to the optical path of the left light receiving system 20L. The illumination light outputted from the left illumination system 10L is reflected by the beam splitter 11L and illuminates the patient's eye E coaxially with the left light receiving system 20L. Similarly, the beam splitter 11R, which couples the optical path of the right illumination system 10R to the optical path of the right light receiving system 20R, is obliquely provided in the right light receiving system 20R for acquiring an image to be presented to the right eye $E_OR$ of the observer.

It is possible to have a configuration so that the position of the illumination light with respect to the optical axis of the light receiving system 20L (20R) is variable. This configuration is realized, for example, by providing a means for changing the projection position of the illumination light onto the beam splitter 11L (11R) like conventional microscopes for ophthalmic surgery.

In the present example, the beam splitter 11L (11R) is disposed between the objective lens 21L (21R) and the patient's eye E. However, the position where the optical path of the illumination light is coupled to the light receiving system 20L (20R) may be an arbitrary position in the light receiving system 20L (20R). Note that the illumination system and the light receiving system may be disposed in a non-coaxial manner. Such a configuration is applied, for example, to the case in which the ophthalmologic microscope system includes a slit lamp microscope.

The present embodiment includes a pair of left and right light receiving systems 20L and 20R. The left light receiving system 20L has a configuration for acquiring an image to be presented to the left eye $E_OL$ of the observer, and the right light receiving system 20R has a configuration for acquiring an image to be presented on the right eye $E_OR$. The left light receiving system 20L and the right light receiving system 20R have the same configuration. The left light receiving system 20L (the right light receiving system 20R) includes the objective lens 21L (21R), the imaging lens 22L (22R), and the image sensor 23L (23R).

It is also possible to employ a configuration in which the imaging lens 22L (22R) is not provided. In the case where the imaging lens 22L (22R) is provided as in the present embodiment, it is possible to form an afocal optical path (a parallel optical path) between the objective lens 21L (21R) and the imaging lens 22L (22R). This makes it easy to dispose an optical element such as a filter, and to dispose an optical path coupling member to couple an optical path from another optical system (in other words, the degree of flexibility and expandability of the optical configuration are improved).

The reference symbol AL1 indicates the optical axis (the objective optical axis) of the objective lens 21L of the left light receiving system 20L, and the reference symbol AR1 indicates the optical axis (the objective optical axis) of the objective lens 21R of the right light receiving system 20R. The image sensor 23L (23R) is, for example, an area sensor such as a CCD image sensor or a CMOS image sensor.

The above is the configuration of the light receiving system 20 when observing the posterior segment (the fundus) of the patient's eye E (see FIG. 1). On the other hand, when observing the anterior eye segment, as shown in FIG.

2, the focus lens 24L (24R) and the wedge prism 25L (25R) are disposed at positions on the patient's eye E side with respect to the objective lens 21L (21R). The focus lens 24L (24R) of the present example is a concave lens and acts to extend the focal length of the objective lens 21L (21R). The wedge prism 25L (25R) changes the direction of the optical path (the objective optical axis AL1 (AR1)) of the left light receiving system 20L (the right light receiving system 20R) outward by a predetermined angle (the deflected optical axes are indicated by the reference symbols AL2 and AR2). In this manner, the focus lens 24L and the wedge prism 25L are disposed in the left light receiving system 20L, and the focus lens 24R and the wedge prism 25R are disposed in the right light receiving system 20R. As a result, the focal position F1 for posterior segment observation is switched to the focal position F2 for anterior segment observation.

A convex lens can be used as the focus lens. In that case, the focus lens is disposed in the optical path at the time of posterior segment observation, and is removed from the optical path at the time of anterior segment observation. Instead of switching the focal length by inserting and removing the focus lens, it is possible to employ a configuration capable of changing the focal length in a continuous or stepwise manner, for example, by providing a focus lens that is movable in the direction along the optical axis.

In the example shown in FIG. 2, the base direction of the wedge prism 25L (25R) is outward (that is, the wedge prism 25L (25R) is disposed in a base-out manner); however, it is possible to apply a wedge prism disposed in a base-in manner. In that case, the wedge prism is disposed in the optical path at the time of observing the posterior eye segment, and is removed from the optical path at the time of observing the anterior eye segment. Instead of switching the direction of the optical path by inserting and removing the wedge prism, the provision of a prism, whose prism amount (and prism direction) is variable, gives a configuration that is capable of changing the direction of the optical path in a continuous or stepwise manner.

The present embodiment includes a pair of left and right eyepiece systems 30L and 30R. The left eyepiece system 30L has a configuration for presenting the image of the patient's eye E acquired by the left light receiving system 20L to the left eye $E_0L$ of the observer, and the right eyepiece system 30R has a configuration for presenting the image of the patient's eye E acquired by the right light receiving system 20R to the right eye $E_0R$. The left eyepiece system 30L and the right eyepiece system 30R have the same configuration. The left eyepiece system 30L (the right eyepiece system 30R) includes the display unit 31L (31R) and the eyepiece lens system 32L (32R).

The display unit 31L (31R) is, for example, a flat panel display such as an LCD. The size of the display surface of the display unit 31L (31R) is, for example, diagonal length of 7 inches or less. The screen sizes of the display devices provided in the pair of the left and right eyepiece systems 30L and 30R are determined under constraints such as the observer's eye width (the pupillary distance, etc.), the size of the apparatus, the design of the apparatus (the disposition of the optical systems and mechanisms, etc.), and the like. That is, there is a trade-off relationship between such constraint conditions and the size of the apparent field of view. From such a viewpoint, the maximum screen size of the display units 31L and 31R is considered to be about 7 inches. By devising the configurations of the eyepiece lens systems 32L and 32R and the disposition of the mechanisms, the display units 31L and 31R that have a screen size exceeding 7 inches can be employed, or the display units 31L and 31R of a small size can be employed.

The interval between the left eyepiece system 30L and the right eyepiece system 30R can be changed. With this, it is possible to adjust the interval between the left eyepiece system 30L and the right eyepiece system 30R according to the eye width of the observer. Further, it is possible to change the relative orientation of the left eyepiece system 30L and the right eyepiece system 30R. That is, the angle formed between the optical axis of the left eyepiece system 30L and the optical axis of the right eyepiece system 30R can be changed. As a result, it becomes possible to induce the convergence of the both eyes $E_0L$ and $E_0R$, thereby being capable of supporting the observer to achieve a stereoscopic view.

The projection system 40 projects light for performing OCT measurement (measurement light) onto the patient's eye E from a direction different from those of the objective optical axes (AL1 and AR1, or, AL2 and AR2) of the light receiving systems 20. In other embodiments, the illumination system may be capable of projecting other light onto the patient's eye in addition to the measurement light for performing OCT. A specific example of other light includes light for a laser treatment (aiming light, laser light for treatment).

The projection system 40 includes the optical scanner 41, the imaging lens 42, the relay lens 43, and the deflection mirror 44. Light from the OCT unit 60 is guided to the optical scanner 41.

The light from the OCT unit 60 (measurement light) is guided through the optical fiber 51 and exits from the end face of the optical fiber 51. The collimator lens 52 is disposed at a position facing the end face of the optical fiber 51. The measurement light, which has been made into a parallel light beam by the collimator lens 52, is led to the optical scanner 41.

The optical scanner 41 is a two dimensional optical scanner and includes the x scanner 41H that deflects light in the horizontal direction (x direction) and the y scanner 41V that deflects light in the vertical direction (y direction). Each of the x scanner 41H and the y scanner 41V may be an optical scanner of an arbitrary type, and, for example, a galvano mirror can be employed for it. The optical scanner 41 is disposed, for example, at the exit pupil position of the collimator lens 52 or in the vicinity of the exit pupil position. In addition, the optical scanner 41 is disposed, for example, at the entrance pupil position of the imaging lens 42 or in the vicinity of the entrance pupil position.

In the case where a two dimensional optical scanner is configured by combining two one dimensional optical scanners as in the present example, the two one dimensional optical scanners are disposed apart from each other by a predetermined distance (for example, about 10 mm). With this, for example, any one dimensional optical scanner can be disposed at the aforementioned exit pupil position and/or at the aforementioned entrance pupil position.

The imaging lens 42 once converges a parallel light beam (measurement light) that has passed through the optical scanner 41. Further, in order to converge the measurement light again at the patient's eye E (at the site to be observed in the fundus or the cornea, or the like), the measurement light is relayed by the relay lens 43 and is reflected toward the patient's eye E by the deflection mirror 44.

The position of the deflection mirror 44 is determined in advance so that the measurement light guided by the projection system 40 is projected onto the patient's eye E from a direction different from those of the objective optical axes (AL1 and AR1, or, AL2 and AR2) of the light receiving systems 20. In the present example, the deflection mirror 44 is disposed at a position between the left light receiving system 20L and the right light receiving system 20R whose objective optical axes are disposed nonparallelly to each other. One of the factors that enables such an arrangement is the improvement of the degree of flexibility in the optical configuration by having disposed the relay lens 43. Further, for example, it is possible to design the distance between the position conjugate with the horizontal optical scanner (the x scanner 41H in the present example) and the objective lenses 21L and 21R to be sufficiently small. This makes it possible to reduce the size of the apparatus.

In general, the scanable area (scannable angle) by the optical scanner 41 is limited. Therefore, the scanable area can be enlarged by employing the imaging lens 42 (or the imaging lens system) whose focal length is variable. Besides, it is also possible to employ any configuration for enlarging the scanable area. Further, a configuration, in which any one or more of the collimator lens 52, the imaging lens 42, and the relay lens 43 is movable along the optical axis, can be employed as an example of a means for changing the focal length (the focal position in the OCT measurement).

The OCT unit 60 includes an interference optical system for performing OCT. FIG. 3 shows an example of the configuration of the OCT unit 60. The optical system shown in FIG. 3 is an example of the swept source OCT. The optical system splits light from a wavelength tunable type (wavelength variable type) light source into measurement light and reference light, generates interference light by superposing the returning light of the measurement light from the patient's eye E and the reference light that has traveled through the reference optical path, and detects the interference light generated. The detection result (detection signal) of the interference light obtained by the interference optical system is a signal indicating a spectrum of the interference light, and is sent to the controller 100.

Like the general swept source OCT apparatus, the light source unit 61 includes a wavelength tunable type light source capable of scanning (sweeping) the wavelength of emitted light. The light source unit 61 temporally changes the output wavelength in the near infrared wavelength band that cannot be visually recognized by human eyes.

The light L0 output from the light source unit 61 is guided to the polarization controller 63 by the optical fiber 62, and the polarization state of the light L0 is adjusted. The light L0, then is guided to the fiber coupler 65 through the optical fiber 64. The fiber coupler 65 splits the light L0 into the measurement light LS and the reference light LR.

The reference light LR is guided to the collimator 67 by the optical fiber 66A. The reference light LR is converted into a parallel light beam by the collimator 67. Then, the reference light LR is guided to the corner cube 70 via the optical path length correction member 68 and the dispersion compensation member 69. The optical path length correction member 68 acts as a delay element for matching the optical path length (optical distance) of the reference light LR and that of the measurement light LS. The dispersion compensation member 69 acts as a dispersion compensation element for matching the dispersion characteristic of the reference light LR and that of the measurement light LS.

The corner cube 70 changes the traveling direction of the reference light LR in the opposite direction. The corner cube 70 is movable in the direction along the incident optical path and the emitting optical path of the reference light LR. With this, the length of the optical path of the reference light LR is changed. It should be noted that it is sufficient to provide any one of a means for changing the length of the optical path of the measurement light LS and a means for changing the length of the optical path of the reference light LR.

The reference light LR that has passed through the corner cube 70 travels through the dispersion compensation member 69 and the optical path length correction member 68, is converted from the parallel light beam into a convergent light beam by the collimator 71, enters the optical fiber 72, is guided to the polarization controller 73. The polarization controller 73 regulates the polarization state of the reference light LR. Subsequently, the reference light LR is guided to the attenuator 75 by the optical fiber 74, and the light amount is adjusted under the control of the controller 100. The reference light LR whose light amount has been adjusted is guided to the fiber coupler 77 by the optical fiber 76.

Meanwhile, the measurement light LS generated by the fiber coupler 65 is guided by the optical fiber 51, is emitted from its fiber end face, and is made into a parallel light beam by the collimator lens 52. The measurement light LS that has been made into the parallel light beam is projected onto the patient's eye E via the optical scanner 41, the imaging lens 42, the relay lens 43, and the deflection mirror 44. The measurement light LS is reflected and scattered at various depth positions of the patient's eye E. The returning light of the measurement light LS from the patient's eye E includes reflected light and backscattered light, advances along the same path as the forward path in the opposite direction, is led to the fiber coupler 65, and then reaches the fiber coupler 77 via the optical fiber 66B.

The fiber coupler 77 generates the interference light by superposing the measurement light LS incident via the optical fiber 66B and the reference light LR incident via the optical fiber 76 with each other (that is, by making the measurement light LS incident through the optical fiber 66B and the reference light LR incident through the optical fiber 76 interfere with each other). The fiber coupler 77 generates a pair of interference light beams LC by splitting the interference light generated from the measurement light LS and the reference light LR at a predetermined branching ratio (for example, 1:1). The pair of interference light beams LC emitted from the fiber coupler 77 are guided to the detector 79 by the optical fibers 78A and 78B, respectively.

The detector 79 is, for example, a balanced photo diode. The balanced photo diode includes a pair of photodetectors that respectively detect the pair of interference light beams LC, and outputs the difference between the detection results obtained by the pair of photodetectors. The detector 79 sends the difference result (detection signal) to the controller 100.

Although the swept source OCT is employed in the present example, it is also possible to employ other types of OCT such as the spectral domain OCT.

The controller 100 executes control of each part of the ophthalmologic microscope system 1 (see FIG. 4). Examples of the control for the illumination system 10 include the followings: turning on of the light source, turning off of the light source, light amount adjustment of the light source; adjustment of the diaphragm; and adjustment of the slit width in the case where slit illumination is possible. Examples of the control for the image sensor 23 include exposure adjustment, gain adjustment, photographing rate adjustment, and the like.

The controller 100 controls the display unit 31 to display various kinds of information. For example, the controller 100 controls the display unit 31L to display an image acquired by the image sensor 23L (or an image generated by processing the image acquired by the image sensor 23L), and controls the display unit 31R to display an image acquired by the image sensor 23R (or an image generated by processing the image acquired by the image sensor 23R).

The controller 100 can control the display unit 31 (the display units 31L and 31R, or other display device) to display information (the scan mode information) representing the pattern of the OCT scan. The scan mode information includes, for example, an image representing a scan area (contour, etc.), information indicating a scan direction (arrow images, etc.), an image representing a scan trajectory, and the like. Further, the controller 100 can display the scan parameter values (scan size, scan interval, scan speed, wavelength, etc.).

The control for the optical scanner 41 is executed, for example, to deflect the measurement light LS in a sequential manner so that the measurement light LS is projected to a plurality of positions according to an OCT scan pattern set in advance.

Parts of the OCT unit 60 to be controlled include the light source unit 61, the polarization controller 63, the corner cube 70, the polarization controller 73, the attenuator 75, and the detector 79.

In addition, the controller 100 controls various mechanisms. As such mechanisms, the stereo angle changing unit 20A, the focusing unit 24A, the optical path deflector 25A, the interval changing unit 30A, and the orientation changing unit 30B are provided.

The stereo angle changing unit 20A relatively rotates the left light receiving system 20L and the right light receiving system 20R. That is, the stereo angle changing unit 20A relatively moves the left light receiving system 20L and the right light receiving system 20R so as to change the angle formed by the respective objective optical axes (for example, AL1 and AR1). This relative movement is performed, for example, in such a manner that the left light receiving system 20L and the right light receiving system 20R are moved by the same angle in the opposite rotation direction. In this movement mode, the orientation of the bisector of the angle formed by the respective objective optical axes (for example, AL1 and AR1) is fixed. On the other hand, it is also possible to perform the aforementioned relative movement so that the orientation of the bisector changes.

The focusing unit 24A inserts and removes the left and right focus lenses 24L and 24R into and from the respective optical paths. The focusing unit 24A may be configured to simultaneously insert and remove the left and right focus lenses 24L and 24R. In another example, the focusing unit 24A may be configured to change the focal position by moving the left and right focus lenses 24L and 24R (simultaneously) in the respective directions along the optical axes. Alternatively, the focusing unit 24A may be configured to change the focal length by (simultaneously) changing the refractive powers of the left and right focus lenses 24L and 24R.

The optical path deflector 25A inserts and removes the left and right wedge prisms 25L and 25R into and from the respective optical paths. The optical path deflector 25A may be configured to simultaneously insert and remove the left and right wedge prisms 25L and 25R. In another example, the optical path deflector 25A may be configured to (simultaneously) change the prism amounts (and the prism directions) of the left and right wedge prisms 25L and 25R to change the respective orientations of the optical paths of the left and right light receiving systems 20L and 20R.

The interval changing unit 30A changes the interval between the left and right eyepiece systems 30L and 30R. The interval changing unit 30A may be configured to relatively move the left and right eyepiece systems 30L and 30R without changing the relative orientations of their optical axes.

The orientation changing unit 30B changes the relative orientations of the left and right eyepiece systems 30L and 30R. The orientation changing unit 30B relatively moves the left eyepiece system 30L and the right eyepiece system 30R so as to change the angle formed by their optical axes. This relative movement is performed, for example, in such a manner that the left eyepiece system 30L and the right eyepiece system 30R are moved by the same angle in the opposite rotation direction. In this movement mode, the orientation of the bisector of the angle formed by the respective optical axes is fixed. On the other hand, it is also possible to perform the aforementioned relative movement so that the orientation of the bisector changes.

The data processor 200 executes various kinds of data processing. Examples of such data processing include a process of forming an image, a process of manipulating (processing) an image, and the like. In addition, the data processor 200 may be capable of executing an analysis process of an image, an analysis process of an examination result, an analysis process of a measurement result, or a process relating to information on a subject (electronic medical record information etc.). The data processor 200 includes the magnification changing unit 210, the condition setting unit 220, and the OCT image forming unit 230.

The magnification changing unit 210 enlarges an image acquired by the image sensor 23. This processing is so-called digital zoom processing, and includes a process of clipping a part of the image acquired by the image sensor 23 and a process of generating an enlarged image of the part clipped. An area of the image to be clipped is set by the observer or by the controller 100. The magnification changing unit 210 applies the same processing to an image (left image) acquired by the image sensor 23L of the left light receiving system 20L and to the image (right image) acquired by the image sensor 23R of the right light receiving system 20R. With this, images of the same magnification are presented to the left eye $E_oL$ and the right eye $E_oR$ of the observer. In this manner, the magnification changing unit 210 functions to change the display magnification of the images to be presented to the observer by processing the output from the image sensor 23 (23L and 23R).

It is possible to provide a so-called optical zoom function in addition to the digital zoom function described above. The optical zoom function is realized by providing a zoom lens (a zoom lens system) in each of the left and right light receiving systems 20L and 20R. As a specific example, the optical zoom function is realized by employing a configuration in which the zoom lenses can be (selectively) inserted into and removed from the respective optical paths, or a configuration in which the zoom lenses can be moved in the directions along the respective optical axes. Control relating to the optical zoom function is executed by the controller 100.

When the display magnification has been changed by the magnification changing unit 210, the information on the change is input to the condition setting unit 220. The condition setting unit 220 sets the projection condition of the measurement light LS based on the information input from the magnification changing unit 210.

The projection condition includes any one or more conditions (parameters) relating to the measurement light LS that is projected onto the patient's eye E. Examples of such conditions include the followings: the size of the scan area with the measurement light LS (the scan size condition); the interval between the projection points of the measurement light LS (the scan interval condition: for example, the interval in the x direction and/or the interval in the y direction); the arrangement pattern of the projection points of the measurement light LS (the scan pattern condition); the positions of the projection points of the measurement light LS in the frame of the image obtained by the image sensor 23 (the scan position condition); the focal position of the measurement light LS (the focal position condition); the measurement depth by the measurement light LS (by the OCT) (the measurement depth condition); the optical characteristics of the measurement light LS (the optical characteristic condition) such as the intensity, the light amount, the duty ratio, the center wavelength, the wavelength width, the spectral distribution, the polarization axis, etc. of the measurement light LS. At least one of these conditions may be included in the projection condition.

The scan size condition is one of the conditions for controlling the optical scanner 41 and indicates the maximum deflection angle of the measurement light LS (that is, the maximum deflection angle of the optical scanner 41 corresponding to the maximum deflection angle of the measurement light LS). The scan size condition includes one or both of a condition indicating the maximum deflection angle in the horizontal direction with the x scanner 41H and a condition indicating the maximum deflection angle in the vertical direction with the y scanner 41V.

The scan interval condition is one of the conditions for controlling the optical scanner 41 and indicates the unit deflection angle of the measurement light LS. That is, the scan interval condition indicates the deflection angle of the optical scanner 41 corresponding to the interval between one projection point of the measurement light LS and a projection point adjacent thereto. The scan interval condition includes one or both of a condition indicating the unit deflection angle with the x scanner 41H and a condition indicating the unit deflection angle with the y scanner 41V. Note that the scan interval condition may include a condition for controlling the light source unit 61 in the OCT unit 60. For example, when the light source unit 61 emits pulsed light, information indicating the light emission rate (the light emission interval, the pulse cycle) may be included in the scan interval condition.

The scan pattern condition is one of the conditions for controlling the optical scanner 41 and shows the shape of the scan trajectory with the measurement light LS. Examples of the scan patterns include the followings: a line scan in which a plurality of projection points are disposed on a line segment; a cross scan in which a plurality of projection points are disposed in a cross shape; a radial scan in which a plurality of projection points are disposed in a radial shape; a circle scan in which a plurality of projection points are disposed in a circle; and a three dimensional scan (a volume scan) in which a plurality of projection points are disposed in lattice points.

The scan position condition is one of the conditions for controlling the optical scanner 41 and indicates the relative position of the OCT scan area with respect to the frame of an image (an observation image) obtained by the image sensor 23. Typically, the center position of the OCT scan area coincides with the center of the frame of the observation image; however, there are cases where it is desired to move the OCT scan area. For example, while observing the optic nerve head and the macula, there are cases where it is desired to perform OCT scans of the macula depicted at a position deviated from the frame center of this observation image. The scan position condition is effective in such a case, for example.

The focal position condition is a condition for controlling a means for changing the focal length (the focal position in OCT measurement) of the optical system that forms the optical path of the measurement light LS (the measurement optical path). In the present embodiment, a mechanism (not shown) that moves any one or more of the collimator lens 52, the imaging lens 42, and the relay lens 43 along the optical axis corresponds to such a focal length changing means.

The measurement depth condition is a condition for controlling a means for changing the measurement depth by the OCT. In the present embodiment, a mechanism (not shown) that moves the corner cube 70 provided in the OCT unit 60 to change the length of the optical path of the reference light LR (the reference optical path) corresponds to such a measurement depth changing means. Note that the measurement depth changing means includes one or both of a means for changing the reference optical path length and a means for changing the measurement optical path length.

The optical characteristic condition is, for example, a condition for controlling any one or more of the followings: the light source unit 61 provided in the OCT unit 60; an optical characteristic changing means provided in the optical path of the light L0 outputted from the light source unit 61; and an optical characteristic changing means provided in the optical path of the measurement light LS. The optical characteristic changing means is, for example, a device for changing the intensity or the like of the light (an attenuator, etc.), a device for changing the light amount, the duty ratio, or the like (a shutter, etc.), an optical element for changing the wavelength characteristic (a filter, etc.), a polarization element for changing the polarization axis, or the like.

An exemplary configuration of the condition setting unit 220 is shown in FIG. 5. The condition setting unit 220 of the present example includes the storage unit 221, the image analysis unit 222, and the condition selection unit 223.

The storage unit 221 stores the association information 221a in advance. In the association information 221a, association relationship between predetermined items and projection conditions is recorded. The predetermined item is an item referred to for setting the projection condition. Examples of the predetermined items include the display magnification of an observation image and the changing amount of the display magnification (e.g., the difference or the ratio between the display magnification before the change and that after the change), and a site of the eye. In addition, the projection condition recorded in the association information 221a is, for instance, one of the above examples.

FIG. 6A shows an example of the association relationship between the display magnification of an observation image and the projection condition. The first association information 221b shown in FIG. 6A is included in the association information 221a. In the first association information 221b, the scan size condition and the scan interval condition, as the projection condition, are associated with the display magnification of the observation image (other projection conditions may also be associated).

The first association information 221b is table information that includes the display magnification columns and the projection condition columns. Various magnification values such as 4 times, 5 times, 6 times, 7 times, . . . are recorded in the display magnification columns. Here, 4 times is the minimum magnification. In the projection condition columns, the scan size value and the scan interval value corresponding to each value of the display magnification are recorded.

In the present example, the scan size value "$A_0$" and the scan interval value "$B_0$" are associated with the minimum magnification of 4 times. The value "$A_0$" of the scan size is set to, for example, 6 mm×6 mm, 9 mm×9 mm, or 9 mm×12 mm (here, [length in the vertical direction]×[length in the horizontal direction]). The value "$B_0$" of the scan interval is set to, for example, 6 mm/511 (when 512 projection points are disposed at equal intervals in a line scan of length 6 mm), 9 mm/1023 (when 1024 projection points are disposed at equal intervals in a line scan of length 9 mm), or 12 mm/1023 (when 1024 projection points are disposed at equal intervals in a line scan of length 12 mm). Here, the quotient value may be rounded to a predetermined place (a predetermined digit). The same applies hereinafter.

In the present example, the scan size value "$A_0$" and the scan interval value "$B_0$" corresponding to the minimum magnification of 4 times are the maximum values, respectively. That is, when the display magnification is more than 4 times, the scan size value and the scan interval value are smaller than "$A_0$" and "$B_0$", respectively. Furthermore, the higher the display magnification, the smaller the scan size value and the scan interval value become. In addition, in the present example, each of the scan size value and the scan interval value is inversely proportional to the display magnification value.

In the case where the first association information 221b is employed, in response to the setting of the display magnification (that is, based on the display magnification after the change), each of the predetermined scan size value and the predetermined scan interval value is selected and employed. Note that in the first association information 221b, one value of each projection condition is associated with each value of the display magnification, but two or more values or an interval may be associated with each value of the display magnification. In addition, the user may arbitrarily change the predetermined value selectively employed.

The format of the first association information 221b is not limited to discrete information such as table information, but may be continuous information such as graph information. Such graph information is, for example, a graph expressed with a two dimensional coordinate system defined by a horizontal axis indicating a continuous value of the display magnification and a vertical axis indicating a continuous value of the projection condition.

FIG. 6B shows an example of the association relationship between the changing amount of the display magnification of an observation image and the projection condition. The second association information 221c shown in FIG. 6B is included in the association information 221a. In the second association information 221c, the scan size condition and the scan interval condition, as the projection condition, are associated with the ratio (e.g., the changing ratio, or, the enlargement ratio/the reduction ratio) which is the changing amount of the display magnification (other projection conditions may also be associated).

The changing ratio of the display magnification is defined, for example, by the ratio between the display magnification before the change and the display magnification after the change. As an example, if the display magnification before the change is 4 times and the display magnification after the change is 6 times, the changing ratio becomes 1.5.

The second association information 221c is table information that includes the columns for the changing ratio of the display magnification and the projection condition columns. Various ratio values such as 1.5, 2.0, 2.5, 3.0, . . . are recorded in the changing ratio columns. In the projection condition columns, the scan size value and the scan interval value corresponding to each changing ratio are recorded.

Note that only the association relationship when the display magnification has been increased is recorded in the second association information 221c; however, in the case where the display magnification has been decreased, it is possible to employ the association relationship that corresponds to the reciprocal of the changing ratio for the decreased display magnification.

Further, in the case where a changing ratio not recorded in the changing ratio columns is applied, the projection condition corresponding to the current changing ratio can be obtained based on the changing ratio value recorded in the second association information 221c. For example, when the display magnification has been changed from 4 times to 7 times, the changing ratio is 1.75. Therefore, the average between the projection condition value corresponding to the changing ratio 1.5 and the projection condition value corresponding to changing ratio of 2.0 can be calculated, and then the average value can be employed as the projection condition value corresponding to the changing ratio 1.75.

In the present example, the larger the changing ratio of the display magnification, the smaller the scan size value and the scan interval value become. In addition, in the present example, each of the scan size value and the scan interval value is inversely proportional to the changing ratio value.

In the case where the second association information 221c is employed, in response to the change of the display magnification (that is, based on the display magnification before the change and the display magnification after the change), each of the predetermined scan size value and the predetermined scan interval value is selectively employed. Note that in the second association information 221c, one value of each projection condition is associated with each value of the changing ratio, but two or more values or an interval may be associated with each value of the changing ratio. In addition, the user may arbitrarily change the predetermined value selectively employed.

The format of the second association information 221c is not limited to discrete information such as table information, but may be continuous information such as graph information. Such graph information is, for example, a graph expressed with a two dimensional coordinate system defined by a horizontal axis indicating a continuous value of the changing ratio of the display magnification and a vertical axis indicating a continuous value of the projection condition.

FIG. 6C shows an example of the association relationship between a site of eye and the projection condition. The third association information 221d shown in FIG. 6C is included in the association information 221a. In the third association information 221d, the scan pattern condition as the projection condition is associated with the site of eye (other projection conditions may also be associated).

The third association information 221d is table information that includes the columns of the site of eye and the projection condition columns. In the columns of the site of eye, various sites of the eye, such as the optic nerve head (ONH) and the macula, are recorded. In the projection condition columns, the scan pattern corresponding to each site is recorded.

In the case where the third association information 221d is applied, in response to the specification of the site of eye depicted in the observation image, the predetermined scan pattern is selected and employed. Note that in the third association information 221d, one scan pattern is associated with each site, but two or more scan patterns may be associated with each site. In addition, the user may arbitrarily change the scan pattern selectively employed.

The association information 221a as described above may be information set as default, or information edited or set arbitrarily by the user. In addition, some sub information (the first to third association information 221b to 221d, etc.) included in the association information 221a may be selectively applied.

When the display magnification has been increased by the magnification changing unit 210, the image analysis unit 222 analyzes an image magnified by the increased display magnification to specify a site of the patient's eye depicted in this magnified image. This image analysis may include feature extraction, pattern recognition, or the like. Specifically, this image analysis may include threshold processing of pixel values (brightness values, RGB values, etc.), filtering, pattern matching, binarization, edge detection, image correction (gamma correction, gradation correction, etc.), image conversion, or the like.

A specific example will be described. When the user zooms in on the optic nerve head while observing the wide area of the fundus of the patient's eye E, this magnified image (a frame of the moving image) is inputted to the image analysis unit 222. The image analysis unit 222 analyzes the brightness values of the pixels of the magnified image to extract a feature area. In the present example, because it is zoomed in on the optic nerve head, an area with high brightness and of a substantially elliptical shape is extracted. As a result, it is specified that the site on which the user zoomed in is the optic nerve head.

Another specific example will be described. When the user zooms in on the macula while observing the wide area of the fundus of the patient's eye E, this magnified image (a frame of the moving image) is inputted to the image analysis unit 222. The image analysis unit 222 analyzes the brightness values of pixels of the magnified image to extract an area with low brightness and of a substantially circular shape. As a result, it is specified that the site on which the user zoomed in is the macula.

The ophthalmologic microscope system 1 can recognize whether the current site to be observed is the anterior eye segment or the eye fundus. For example, the controller 100 can determine whether the current site to be observed is the anterior eye segment or the eye fundus based on any of the followings: whether or not the front lens 90 is used; whether or not the focus lenses 24L and 24R are disposed in the optical path; and whether or not the wedge prisms 25L and 25R are disposed in the optical path. The image analysis unit 222 can specify the site by referring to the result of the determination. For example, when the current site to be observed is the anterior eye segment and when an area with low brightness and of a substantially circular shape is extracted from the magnified image, the image analysis unit 222 determines that the extracted area corresponds to the pupil (and the iris). On the other hand, when the current site to be observed is the eye fundus and when an area with low brightness and of a substantially circular shape is extracted from the magnified image, the image analysis unit 222 determines that the extracted area corresponds to the macula.

The condition selection unit 223 selects, from the association information 221a (the third association information 221d), a scan pattern that is associated with the site specified by analyzing the magnified image by the image analysis unit 222. For example, when the site specified by the image analysis unit 222 is the optic nerve head, the condition selection unit 223 acquires, from the third association information 221d, the circle scan which is the scan pattern associated with the optic nerve head. Alternatively, when the site specified by the image analysis unit 222 is the macula, the condition selection unit 223 acquires, from the third association information 221d, the three dimensional (3D) scan which is the scan pattern associated with the macula.

The OCT image forming unit 230 forms an image of the patient's eye E based on the result of the detection of the interference light LC obtained by the detector 79 of the OCT unit 60. The controller 100 sends detection signals sequentially outputted from the detector 79 to the OCT image forming unit 230. The OCT image forming unit 230 applies Fourier transform etc. to the spectral distribution formed based on the detection results obtained by the detector 79 for each series of wavelength scans (for each A line), thereby forming the reflection intensity profile for each A line. In addition, the OCT image forming unit 230 forms image data by applying an imaging process to each A line profile. With this, a B scan image (a cross sectional image), volume data (three dimensional image data), or the like is obtained.

The data processor 200 may have a function of analyzing an image (an OCT image) formed by the OCT image forming unit 230. Examples of such an analysis function include retinal thickness analysis, comparative analysis with normal eyes, and the like. Such an analysis function is executed using a known application. Further, the data processor 200 may have a function of analyzing an image acquired by the light receiving system 20. In addition, the data processor 200 may have an analysis function that is a combination of the analysis of an image acquired by the light receiving system 20 and the analysis of an OCT image.

The user interface (UI) 300 has a function for exchanging information between the observer or the like and the ophthalmologic microscope system 1. The user interface 300 includes a display device and an operation device (an input device). The display device may include the display unit 31 and may include other display devices. The operation device includes various hardware keys and/or various software keys. It is possible to integrate at least part of the operation devices and at least part of the display devices. A touch panel display is one example of such an integrated configuration.

The communication unit 400 performs a process of sending information to other apparatuses and a process of receiving information sent from other apparatuses. The communication unit 400 may include a communication device conforming to a predetermined network (LAN, Internet, etc.). For example, the communication unit 400 acquires information from an electronic medical record database or a medical image database via a LAN provided in a medical institution. In the case where an external monitor is provided, the communication unit 400 can send an image acquired by the ophthalmologic microscope system 1 (e.g., an image acquired by the light receiving system 20, an OCT image) to the external monitor substantially in real time.

Figure 7:
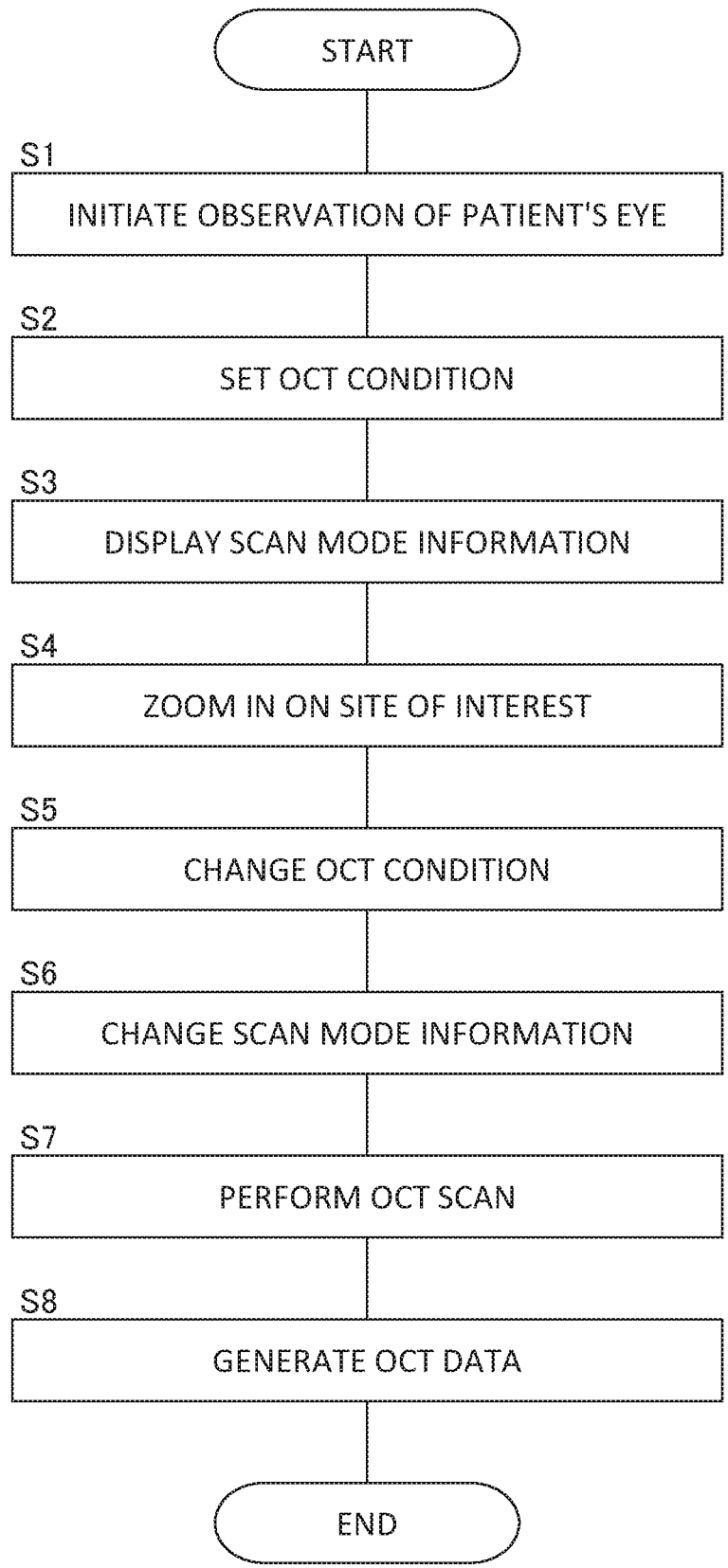
FIG. 7 is a flowchart illustrating an example of the usage mode of the ophthalmologic microscope system according to the embodiment.

The usage mode of the ophthalmologic microscope system of the present embodiment will be described. FIG. 7 shows an example of the usage mode of the ophthalmologic microscope system.

When the user performs a predetermined operation, the controller 100 controls the left and right illumination systems 10L and 10R to initiate projecting the illumination light onto the patient's eye E. At the same time, the controller 100 controls the left and the right display units 31L and 31R to display the images obtained by the left and the right image sensors 23L and 23R, respectively. As a result, the user can perform binocular observation (stereoscopic observation) of the patient's eye E via the left and right eyepiece systems 30L and 30R.

The user operates the left and right light receiving systems 20L and 20R so as to obtain a desired observation field. At this time, the observation magnification (the magnification of the images displayed on the display units 31L and 31R) is also adjusted. The observation magnification is changed by the digital zoom (by the magnification changing unit 210).

Next, the OCT conditions (the projection condition of the measurement light LS, the condition of the OCT unit 60, etc.) is set. This condition setting includes at least one of manual setting performed by the user, automatic setting of default condition (initial condition), and automatic setting executed by the condition setting unit 220. The automatic setting by the condition setting unit 220 is executed, for example, based on the observation magnification set in the step S1. Specifically, the condition selection unit 223 of the condition setting unit 220 selects the projection condition corresponding to the magnification set in the step S1 from the association information 221a (e.g., the first association information 221b). The selected projection condition is employed.

At this stage, live OCT can be started. The live OCT is an imaging modality that acquires a moving image of a certain cross section of the patient's eye E by repeating OCT measurement of a predetermined scan pattern. Alternatively, the OCT measurement may be performed in response to an instruction from the user or the controller 100.

The controller 100 displays the scan mode information representing the mode of the OCT conditions set in the step S2. For example, the scan mode information is superimposed on the observation images of the patient's eye E displayed on the display units 31L and 31R (overlay display).

Figure 8A:
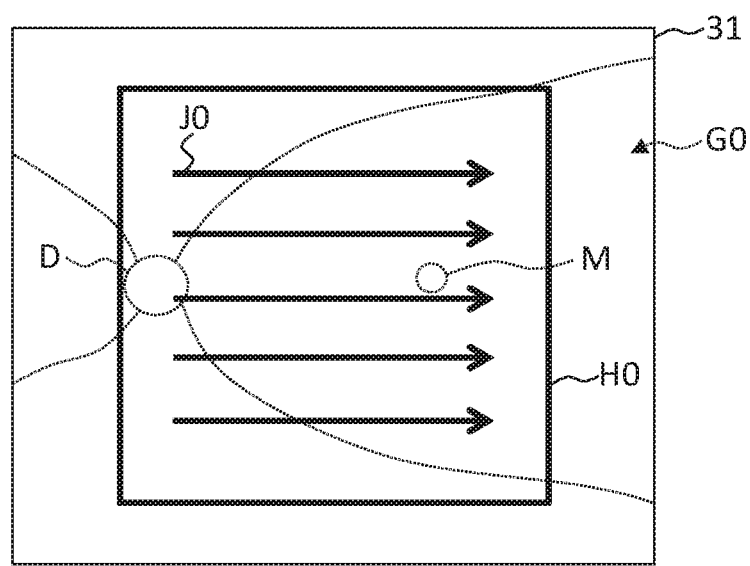
FIG. 8A is a schematic diagram for describing the usage mode of the ophthalmologic microscope system according to the embodiment.

An example of the overlay display is shown in FIG. 8A. The reference symbol G0 indicates an observation image displayed on the display unit 31 (31L or 31R). The observation image G0 is a fundus image of the patient's eye E, and is a wide area image depicting an area including the optic nerve head D and the macula M. It is assumed that the scan pattern set in the step S2 is the three dimensional scan. The controller 100 superimposes, on the observation image G0, the area image H0 indicating (the contour of) an area of the three dimensional scan and the direction images J0 indicating the directions of a plurality of line scans included in the three dimensional scan.

In order to observe the site of interest at higher magnification, the user performs the operation for moving the light receiving systems 20L and 20R, the operation for magnification change. The magnification change processing is executed by the magnification changing unit 210 (the digital zoom).

Information indicating the magnification changed in the step S4 is inputted to the condition setting unit 220 (the condition selection unit 223). The condition selection unit 223 selects the projection condition corresponding to the inputted information from the association information 221a. For example, when the inputted information includes the magnification value after the change, the condition selection unit 223 can select the projection condition corresponding to the magnification value from the first association information 221b. In another example, when the inputted information includes the change content of the magnification (for example, the magnification value before the change and the magnification value after the change), the condition selection unit 223 calculates the changing ratio of the magnification from this change content, and selects the projection condition corresponding to the changing ratio from the second association information 221c.

The projection condition selected by the condition selection unit 223 is sent to the controller 100. The controller 100 specifies the condition of the same item as the projection condition selected by the condition selection unit 223, from among the current OCT conditions (the OCT conditions set in the step S2). Further, the controller 100 replaces the specified current condition with the newly selected projection condition. As a result, at least part of the OCT conditions set in the step S2 is changed.

The controller 100 changes the scan mode information, which represents the OCT conditions set in the step S2, displayed in the step S3 to scan mode information that represents the pattern of the OCT conditions newly set in the step S5. The new scan mode information is also displayed over the observation image.

Figure 8B:
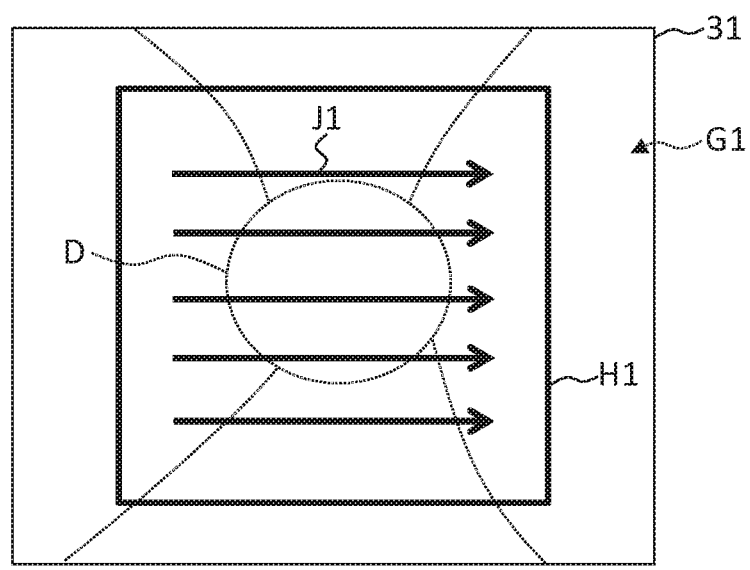
FIG. 8B is a schematic diagram for describing the usage mode of the ophthalmologic microscope system according to the embodiment.

An example of such new overlay display is shown in FIG. 8B. The reference symbol G1 indicates an observation image after the magnification change displayed on the display unit 31 (31L or 31R). The observation image G1 is a magnified image in which the optic nerve head D is the site of interest. The reference symbol H1 is an area image showing (the contour of) an area of the three dimensional scan with the scan size set in the step S5. Further, the reference symbol J1 is the direction images showing the directions of a plurality of line scans included in the new three dimensional scan. Note that in the present example, the scan pattern is not changed. The case in which the scan pattern is also changed will be described later.

The controller 100 controls the OCT unit 60, the optical scanner 41, etc. based on the OCT conditions including the projection condition set in the step S5 to perform the OCT scan of the patient's eye E. In the examples shown in FIG. 8A and FIG. 8B, the OCT scan is applied to the optic nerve head D and its vicinity.

For example, it is assumed that the magnification of the image G1 shown in FIG. 8B is 3 times the magnification of the image G0 shown in FIG. 8A. In this case, the area (dimension) indicated by the area image H1 is "⅓×⅓" times the area (dimension) indicated by the area image H0. Furthermore, the scan interval of the three dimensional scan in the region indicated by the area image H1 is ⅓ of the scan interval of the three dimensional scan in the region indicated by the area image H0. In this way, it is possible to scan a narrower area with higher density when the magnification of the observation image is increased.

The OCT image forming unit 230 forms an image based on the data collected by the OCT scan in the step S7. Further, the data processor 200 can generate analysis data by analyzing this image. The OCT data acquired (images, analysis data, etc.) is displayed on the display units 31L and 31R, for example.

The usage mode that also performs the scan pattern setting as well as the scan size setting and the scan interval setting will be described. In the present example, in addition to the processing described in the step S5 above, the scan pattern setting is performed. The setting of scan pattern is performed in the following manner, for example.

When the magnification of the observation image is changed in the step S4, the observation image (a frame of the moving image) is inputted to the image analysis unit 222. By analyzing the observation image inputted, the image analysis unit 222 specifies the site of the patient's eye E depicted in the observation image. Information indicating the site specified (the name of the site, the identification information, etc.) is inputted to the condition selection unit 223. The condition selection unit 223 selects the scan pattern corresponding to the site specified by the image analysis unit 222, from the third association information 221d (FIG. 6C).

Information indicating the scan pattern selected by the condition selection unit 223 is sent to the controller 100. The controller 100 replaces the scan pattern in the current OCT conditions with the scan pattern newly selected. This is an additional process executed in the step S5.

Figure 8C:
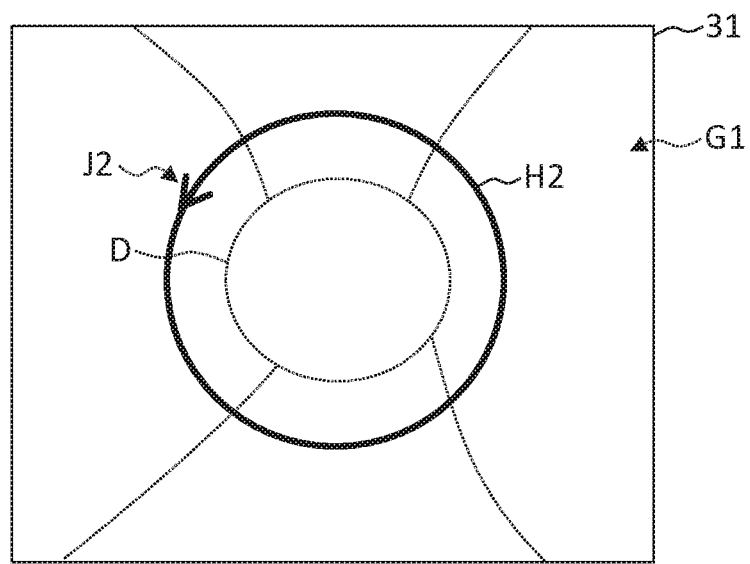
FIG. 8C is a schematic diagram for describing the usage mode of the ophthalmologic microscope system according to the embodiment.

Further, based on the OCT conditions (the projection condition) changed in the step S5, the controller 100 changes the scan mode information overlaid on the observation image. An example of this new overlay display is shown in FIG. 8C. The observation image G1 is the same as that in the case of FIG. 8B, and is a magnified image in which the optic nerve head D is the site of interest. The image analysis unit 222 analyzes the observation image G1 to determine that the optic nerve head is depicted in it. By referring to the third association information 221d, the condition selection unit 223 specifies the circle scan as the scan pattern corresponding to the optic nerve head.

The reference symbol H2 is a trajectory image showing the trajectory of the circle scan having a predetermined scan size. Further, the reference symbol J2 is the direction image showing the direction of the circle scan. The size (diameter) of the circle scan is set to the scan size set in the step S5, for example. Alternatively, the size of the circle scan can be determined based on the size of the optic nerve head D. Also, the position of the circle scan is set by an arbitrary method. For example, the center of the circle scan is made to coincide with the center of the optic nerve head D (e.g., the center of the approximate ellipse of the optic nerve head D). The scan interval in the circle scan may be set in the step S5.

Actions and effects of the ophthalmologic microscope system of the present embodiment will be described.

The ophthalmologic microscope system of the present embodiment includes an illumination system (10, 10L, 10R), a light receiving system (20L, 20R), a display controller (the controller 100), a magnification changing unit (210), an interference optical system (the OCT unit 60), an optical scanner (41), an OCT data generation unit (the data processor 200, the OCT image forming unit 230), a condition setting unit (220), and an OCT controller (the controller 100).

The illumination system is configured to project illumination light onto a patient's eye. The light receiving system is configured to guide returning light of the illumination light that has been projected onto the patient's eye to an image sensor (23, 23L, 23R). Here, the image sensor may be an external device connected to the ophthalmologic microscope system. The display controller is configured to display an image (an observation image) based on an output from the image sensor on a display means (the display units 31, 31L, 31R, the user interface 300, etc.). Here, the display means may be an external device connected to the ophthalmologic microscope system. The magnification changing unit is configured to change the display magnification of the image (the observation image) by processing the output from the image sensor. The interference optical system is configured to split light from an OCT light source (the light source unit 61) into measurement light (LS) and reference light (LR), and to detect interference light (LC) generated from returning light of the measurement light from the patient's eye and the reference light. The optical scanner is configured to scan the patient's eye with the measurement light. The OCT data generation unit is configured to process a detection result of the interference light to generate data (an image, analysis data, etc.). The condition setting unit is configured to set a projection condition of the measurement light in accordance with change in the display magnification performed by the magnification changing unit. The OCT controller controls at least one of the interference optical system and the optical scanner based on the projection condition set, thereby having an OCT scan to be performed on the patient's eye.

According to such an embodiment, the projection condition for the OCT scan can be automatically set based on the magnification of the digital zoom of the observation image by the magnification changing unit. Therefore, the user does not need to perform a complicated operation for setting the projection condition.

The projection condition that is automatically set by the condition setting unit may include any of the following conditions: a scan size condition indicating the size of a scan area with the measurement light; a scan interval condition indicating an interval between projection points of the measurement light; and a scan pattern condition indicating an arrangement pattern of projection points of the measurement light.

When the scan size condition has been set, the OCT controller controls the optical scanner based on the scan size condition. With this, it is possible to perform the OCT scan in the area automatically set according to the change in the magnification of the observation image.

In the case where the present example is employed, when the display magnification has been increased by the magnification changing unit, the condition setting unit can set the scan size condition so that the size of the scan area is reduced. As a result, it becomes possible to smoothly acquire an OCT image for the area suitable for the site being observed at high magnification. Conversely, when the display magnification has been lowered by the magnification changing unit, the condition setting unit can set the scan size condition so that the size of the scan area is increased.

When the scan interval condition has been set, the OCT controller controls the optical scanner based on the scan interval condition set. As a result, it is possible to perform the OCT scan at the automatically set density according to the change in the magnification of the observation image.

In the case where the present example is employed, when the display magnification has been increased by the magnification changing unit, the condition setting unit can set the scan interval condition so that the interval of the projection points of the measurement light is reduced. As a result, it is possible to smoothly acquire a high-definition OCT image relating to the site being observed at high magnification. Conversely, when the display magnification has been lowered by the magnification changing unit, the condition setting unit can set the scan interval condition so that the interval of the projection points of the measurement light is increased.

When the scan pattern condition has been set, the OCT controller controls the optical scanner based on the scan pattern condition set. As a result, it is possible to perform the OCT scan with a pattern automatically set according to the change in the magnification of the observation image.

In the case where the present example is employed, the condition setting unit (220) may include a storage unit (221), an image analysis unit (222), and a condition selection unit (223). The storage unit stores, in advance, association information (the third association information 221d) in which a scan pattern is associated with each of one or more sites of an eye. When the display magnification has been increased by the magnification changing unit, the image analysis unit analyzes an image magnified by the increased display magnification, to specify a site of the patient's eye depicted in this image. The condition selection unit selects a scan pattern associated with the site specified by the image analysis unit, from the association information. The selected scan pattern is used to control the optical scanner. According to such a configuration, it is possible to automatically select a scan pattern corresponding to the site being observed at high magnification, and to perform the OCT scan. Conversely, it is also possible to employ a configuration so that the scan pattern is automatically set when the display magnification has been lowered by the magnification changing unit.

It should be noted that the projection condition that can be automatically set according to the embodiment is not limited to those described above. For example, it is possible to employ a configuration so that any of the following projection conditions and the like is automatically set: a scan position condition indicating the position of the projection points of the measurement light within the frame of an image (an observation image) obtained by the image sensor; a focal position condition indicating the focal position of the measurement light; a measurement depth condition indicating the measurement depth by the measurement light (by OCT); and an optical characteristic condition indicating an optical characteristic of the measurement light.

In the embodiment, the display controller can display information (the scan mode information) indicating the projection condition set by the condition setting unit together with the observation image. According to such a configuration, it is possible to present to the user what kind of projection condition has been set. Information indicating the projection condition is overlaid on the observation image, for example. As a result, the user can check the projection condition while observing the patient's eye with the microscope. In particular, the user can easily and intuitively grasp information such as the area of the patient's eye to which the OCT scan is to be applied, the direction of the OCT scan to be performed, and the density of the OCT scan to be performed.

The embodiment described above is merely an example for implementing the present invention. Those who intend to implement the present invention may apply any modification, omission, addition, substitution, etc. within the scope of the gist of the present invention.

In the embodiment described above, the switching between the fundus observation and the anterior eye segment observation is performed by inserting and removing the focus lenses 24L and 24R and the wedge prisms 25L and 25R into and from the respective optical paths of the light receiving systems 20. More specifically, at the time of fundus observation, these optical elements are removed from the optical path, and at the time of anterior eye segment observation, these optical elements are disposed in the optical path. With such an insertion and removal of these optical elements, the focal length and the orientations of the objective optical axes are switched.

Figure 9:
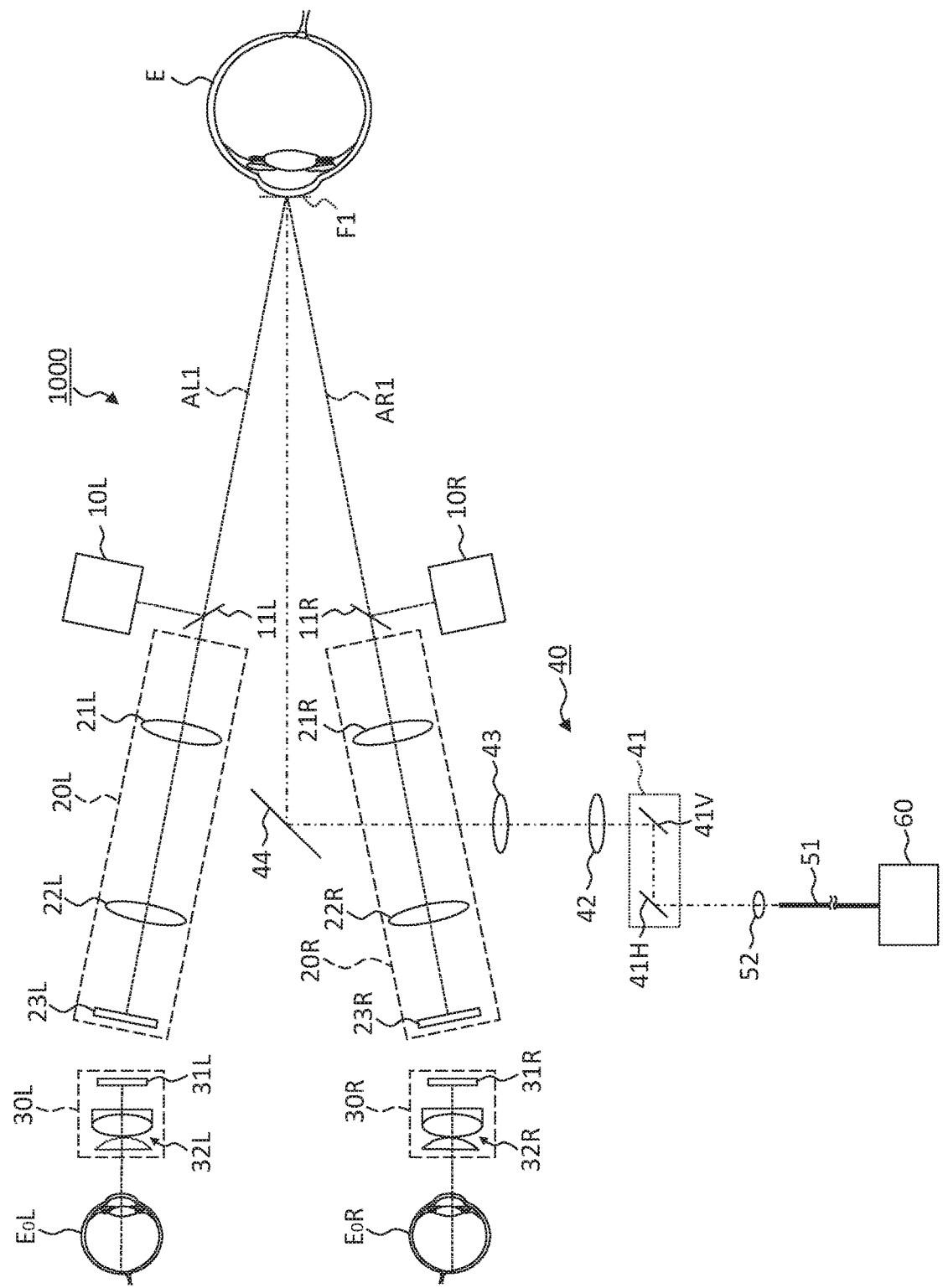
FIG. 9 is a schematic diagram illustrating an example of the configuration of the ophthalmologic microscope system according to the modification example.
Figure 10:
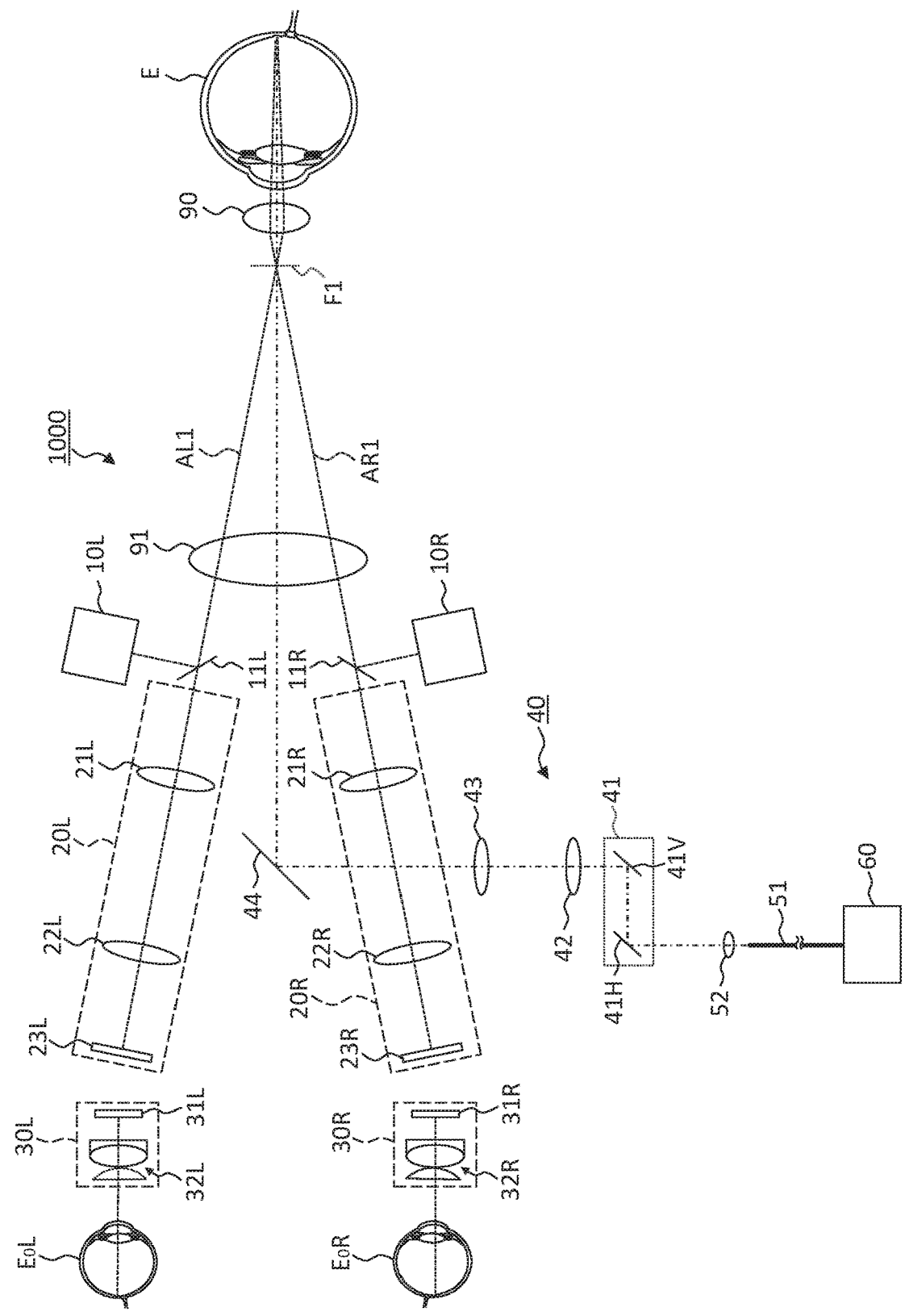
FIG. 10 is a schematic diagram illustrating an example of the configuration of the ophthalmologic microscope system according to the modification example.

FIG. 9 and FIG. 10 show a modification example for realizing such a switching of observation sites. FIG. 9 shows the state of the ophthalmologic microscope system 1000 at the time of observing the anterior eye segment, and FIG. 10 shows the state at the time of observing the eye fundus. The ophthalmologic microscope system 1000 includes the illumination systems 10L and 10R, the light receiving systems 20L and 20R, the eyepiece systems 30L and 30R, the illumination system 40, and the OCT system 60, each of which is similar to that in the embodiment described above. The same reference symbols are given to the same elements as those in the embodiment described above, and the description thereof is omitted.

At the time of observing the anterior eye segment, as shown in FIG. 9, the anterior segment (for example, the anterior surface of the cornea) of the patient's eye E is disposed at the focal position F1 of the light receiving systems 20L and 20R. On the other hand, at the time of observing the eye fundus, as shown in FIG. 10, the front lens 90 and the optical path length conversion lens 91 are disposed in the optical paths of the light receiving systems 20L and 20R. The front lens 90 is an optical element similar to that of the embodiment described above, and is disposed between the focal position F1 and the patient's eye E. The optical path length conversion lens 91 is disposed at a position between the beam splitter 11L, which couples the optical path of the illumination system 10L to the optical path of the light receiving system 20L, and the focal position F1, and at a position between the beam splitter 11R, which couples the optical path of the illumination system 10R to the optical path of the light receiving system 20R, and the focal position F1. In the present example, a single optical path length conversion lens 91 is disposed so as to extend over the optical paths of both the light receiving systems 20L and 20R. However, separate optical elements may be disposed for the respective light receiving systems 20L and 20R.

According to the present modification example, by applying the optical path length conversion lens 91, it is possible to perform eye fundus observation from the same position for anterior eye segment observation, without changing the distance between the light receiving systems 20L and 20R and (the cornea of) the patient's eye E.

What is claimed is:

1. An ophthalmologic microscope system comprising:
    an illumination system configured to project illumination light onto a patient's eye;
    a light receiving system configured to guide returning light of the illumination light that has been projected onto the patient's eye to an image sensor;
    a display controller configured to control a display device to display an image based on an output from the image sensor;
    a magnification changing unit executed on a processor, the magnification changing unit configured to change display magnification of the image by processing the output from the image sensor;
    an interference optical system configured to split light from an OCT light source into measurement light and reference light, project the measurement light onto the patient's eye via an optical scanner, and detect interference light generated from returning light of the measurement light from the patient's eye and the reference light;
    an OCT data generation unit executed on a processor, the OCT data generation unit configured to process a detection result of the interference light to generate data;
    a condition setting unit executed on a processor, the condition setting unit configured to set a projection condition of the measurement light in accordance with change in the display magnification performed by the magnification changing unit; and
    an OCT controller configured to control at least one of the interference optical system and the optical scanner based on the projection condition set, wherein, the interference optical system includes a focal position changing member configured to change a focal position of the measurement light, the projection condition includes a focal position condition that is a condition of the focal position, the condition setting unit sets the focal position condition in accordance with the change in the display magnification, and the OCT controller controls the focal position changing member based on the focal position condition set by the condition setting unit.

2. The ophthalmologic microscope system of claim 1, wherein
the condition setting unit sets a scan size condition indicating a size of a scan area with the measurement light, and
the OCT controller controls the optical scanner based on the scan size condition.

3. The ophthalmologic microscope system of claim 2, wherein when the display magnification has been increased by the magnification changing unit, the condition setting unit sets the scan size condition to reduce the size of the scan area.

4. The ophthalmologic microscope system of claim 1, wherein
the condition setting unit sets a scan interval condition indicating an interval between projection points of the measurement light, and
the OCT controller controls the optical scanner based on the scan interval condition.

5. The ophthalmologic microscope system of claim 4, wherein when the display magnification has been increased by the magnification changing unit, the condition setting unit sets the scan interval condition to reduce the interval of the projection points.

6. The ophthalmologic microscope system of claim 1, wherein
the condition setting unit sets a scan pattern condition indicating an arrangement pattern of projection points of the measurement light, and
the OCT controller controls the optical scanner based on the scan pattern condition.

7. The ophthalmologic microscope system of claim 6, wherein the condition setting unit comprises:
a storage unit, executed on a processor, the storage unit pre-storing, association information in which a scan pattern is associated with each of one or more sites of an eye,
an image analysis unit, executed on a processor, the image analysis unit configured to analyze, when the display magnification has been increased by the magnification changing unit, an image magnified by the increased display magnification to specify a site of the patient's eye depicted in this image, and
a condition selection unit configured to select a scan pattern associated with a specified site from the association information.

8. The ophthalmologic microscope system of claim 1, wherein the display controller displays information indicating the projection condition set by the condition setting unit together with the image.

9. The ophthalmologic microscope system of claim 1, further comprising a pair of light receiving systems, wherein
the pair of the light receiving systems each comprises an objective lens and an image sensor, wherein objective optical axes of which are disposed in a mutually nonparallel manner, and the pair of the light receiving systems are configured to guide returning light of the illumination light that has been projected onto the patient's eye to respective image sensors via respective objective lenses, and
the measurement light is projected onto the patient's eye from a direction different from the objective optical axes.

10. The ophthalmologic microscope system of claim 2, wherein
the condition setting unit sets a scan interval condition indicating an interval between projection points of the measurement light, and
the OCT controller controls the optical scanner based on the scan interval condition.

11. The ophthalmologic microscope system of claim 3, wherein
the condition setting unit sets a scan interval condition indicating an interval between projection points of the measurement light, and
the OCT controller controls the optical scanner based on the scan interval condition.

12. The ophthalmologic microscope system of claim 2, wherein
the condition setting unit sets a scan pattern condition indicating an arrangement pattern of projection points of the measurement light, and
the OCT controller controls the optical scanner based on the scan pattern condition.

13. The ophthalmologic microscope system of claim 3, wherein
the condition setting unit sets a scan pattern condition indicating an arrangement pattern of projection points of the measurement light, and
the OCT controller controls the optical scanner based on the scan pattern condition.

14. The ophthalmologic microscope system of claim 4, wherein
the condition setting unit sets a scan pattern condition indicating an arrangement pattern of projection points of the measurement light, and
the OCT controller controls the optical scanner based on the scan pattern condition.

15. The ophthalmologic microscope system of claim 5, wherein
the condition setting unit sets a scan pattern condition indicating an arrangement pattern of projection points of the measurement light, and
the OCT controller controls the optical scanner based on the scan pattern condition.

16. The ophthalmologic microscope system of claim 2, wherein the display controller displays information indicating the projection condition set by the condition setting unit together with the image.

17. The ophthalmologic microscope system of claim 3, wherein the display controller displays information indicating the projection condition set by the condition setting unit together with the image.

18. The ophthalmologic microscope system of claim 2, further comprising a pair of light receiving systems, wherein
the pair of the light receiving systems each comprises an objective lens and an image sensor, wherein objective optical axes of which are disposed in a mutually nonparallel manner, and the pair of the light receiving systems are configured to guide returning light of the illumination light that has been projected onto the patient's eye to respective image sensors via respective objective lenses, and the measurement light is projected onto the patient's eye from a direction different from the objective optical axes.

19. The ophthalmologic microscope system of claim 3, further comprising a pair of light receiving systems, wherein
the pair of the light receiving systems each comprises an objective lens and an image sensor, wherein objective optical axes of which are disposed in a mutually nonparallel manner, and the pair of the light receiving systems are configured to guide returning light of the illumination light that has been projected onto the patient's eye to respective image sensors via respective objective lenses, and
the measurement light is projected onto the patient's eye from a direction different from the objective optical axes.

20. The ophthalmologic microscope system of claim 4, further comprising a pair of light receiving systems, wherein
the pair of the light receiving systems each comprises an objective lens and an image sensor, wherein objective optical axes of which are disposed in a mutually nonparallel manner, and the pair of the light receiving systems are configured to guide returning light of the illumination light that has been projected onto the patient's eye to respective image sensors via respective objective lenses, and
the measurement light is projected onto the patient's eye from a direction different from the objective optical axes.

21. The ophthalmologic microscope system of claim 1, wherein
the interference optical system further includes a measurement depth changing member configured to change an OCT measurement depth,
the projection condition further includes a measurement depth condition that is a condition of the OCT measurement depth,
the condition setting unit further sets the measurement depth condition in accordance with the change in the display magnification, and
the OCT controller further controls the measurement depth changing member based on the measurement depth condition set by the condition setting unit.

22. The ophthalmologic microscope system of claim 1, wherein
the interference optical system further includes an optical characteristic changing member configured to change an optical characteristic of the measurement light,
the projection condition further includes an optical characteristic condition that is a condition of the optical characteristic,
the condition setting unit further sets the optical characteristic condition in accordance with the change in the display magnification, and
the OCT controller further controls the optical characteristic changing member based on the optical characteristic condition set by the condition setting unit.

* * * * *